United States Patent [19]
Melendez et al.

[11] Patent Number: 6,024,923
[45] Date of Patent: *Feb. 15, 2000

[54] INTEGRATED FLUORESCENCE-BASED BIOCHEMICAL SENSOR

[75] Inventors: Jose Melendez, Plano; Richard A. Carr, Rowlett; Diane Arbuthnot, Plano, all of Tex.

[73] Assignee: Texas Instruments Incorporated, Dallas, Tex.

[ * ] Notice: This patent is subject to a terminal disclaimer.

[21] Appl. No.: 09/313,466

[22] Filed: May 17, 1999

Related U.S. Application Data

[63] Continuation of application No. 08/942,090, Oct. 1, 1997, Pat. No. 5,922,285
[60] Provisional application No. 60/027,287, Oct. 1, 1996.
[51] Int. Cl.[7] .................................................. G01N 21/64
[52] U.S. Cl. .......................... 422/82.08; 422/91; 436/165
[58] Field of Search .................... 422/82.05, 82.08, 422/82.11, 91; 436/68, 136, 138, 165, 172

[56] References Cited

U.S. PATENT DOCUMENTS

| | | |
|---|---|---|
| 4,368,047 | 1/1983 | Andrade et al. . |
| 5,517,313 | 5/1996 | Colvin, Jr. . |
| 5,545,567 | 8/1996 | Gretillat et al. . |
| 5,580,794 | 12/1996 | Allen ........................................ 436/169 |
| 5,589,136 | 12/1996 | Northrup et al. ........................ 422/102 |
| 5,614,726 | 3/1997 | Kaye et al. . |
| 5,633,724 | 5/1997 | King et al. . |
| 5,738,992 | 4/1998 | Cook et al. . |
| 5,738,997 | 4/1998 | Hayashi et al. . |

FOREIGN PATENT DOCUMENTS 0 685 730 A1  12/1995  European Pat. Off. .

OTHER PUBLICATIONS

MacCraith et al., "Light–emitting–diode–based oxygen sensing using evanescent wave excitation of a dye–doped sol–gel coating," Optical Engineering, vol. 33, No. 12, Dec. 1994, pp. 3861–3866.

*Primary Examiner*—Jeffrey Snay
*Attorney, Agent, or Firm*—David Denker; Robby T. Holland; Richard L. Donaldson

[57] ABSTRACT

An integrated biochemical sensor (200) for detecting the presence of one or more specific samples (240) having a device platform (355) with a light absorbing upper surface and input/output pins (375) is disclosed. An encapsulating housing (357) provides an optical transmissive enclosure which covers the platform (355) and has a layer of fluorescence chemistry on its outer surface (360). The fluorophore is chosen for its molecular properties in the presence of the sample analyte (240). The detector (370), light sources (365, 367, 407, 409) are all coupled to the platform (355) and encapsulated within the housing (357). A filter (375) element is used to block out unwanted light and increase the detector's (370) ability to resolve wanted emission light.

9 Claims, 3 Drawing Sheets

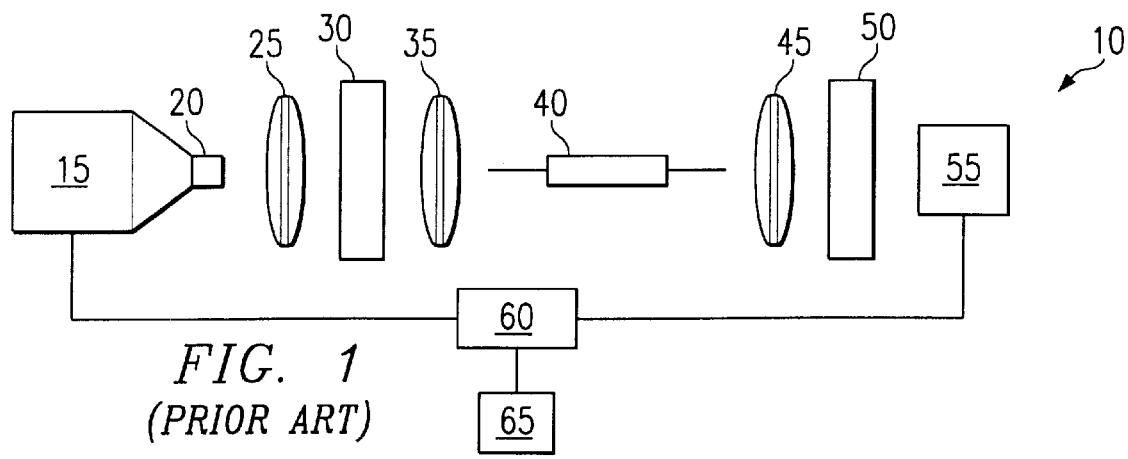
FIG. 1
*(PRIOR ART)*
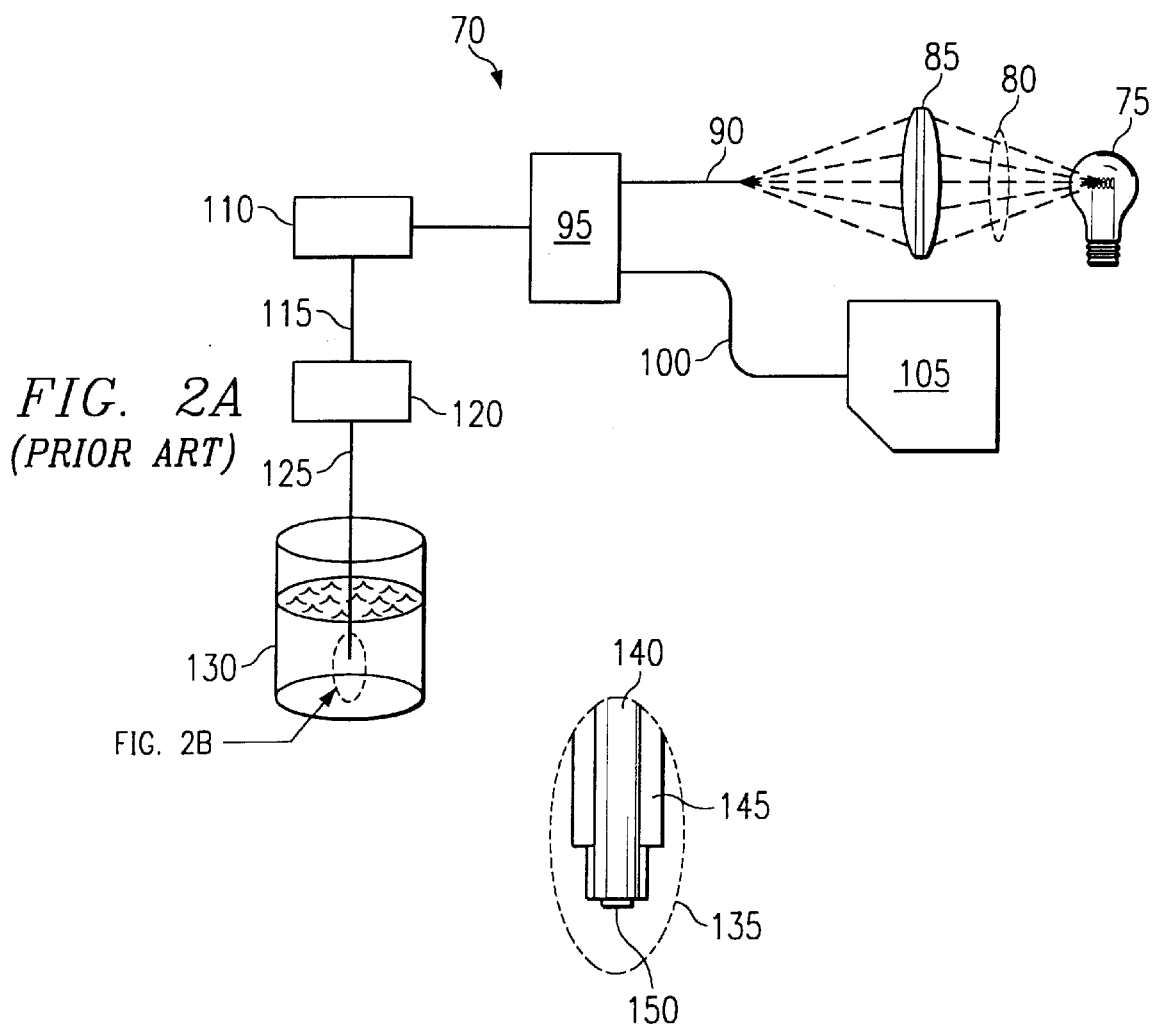
FIG. 2A
*(PRIOR ART)*
FIG. 2B
*(PRIOR ART)*

INTEGRATED FLUORESCENCE-BASED BIOCHEMICAL SENSOR

This application is a continuation of U.S. application Ser. No. 08/942,090 filed Oct. 1, 1997, now issued as U.S. Pat. No. 5,922,285, which claims the benefit of provisional application No. 60/027,287 filed Oct. 1, 1996.

TECHNICAL FIELD

The present invention relates in general to the field of optical sensors and in particular to an integrated biochemical sensor that uses fluorescence chemistries to detect the presence of substances which interact with the chemistries.

BACKGROUND OF THE INVENTION

Without limiting the scope of the invention, its background is described in connection with a fluoroluminescence sensor using a coated article, such as a fiber optic cable, that is immersed in a sample solution.

The use of fluorescence based technology to detect sample gases and liquids has been known for some time now. A typical application involves the molecular labeling of a thin film, cable or other article followed by excitation and fluorescent measurement in the presence of the particular sample of interest. Fluorescent labeling involves the deposit of a suitable fluorescence chemistry known to interact with the sample of interest. A source of excitation light is directed at the coated article which when brought in contact with the sample emits a low intensity fluorescence energy. A light detector can be used to measure the emission and detect the presence of the sample. These processes can also be modified to work on solids.

A known prior art system uses a fluorescence-based fiber optic oxygen sensor with a single high brightness Light Emitting Diode (LED). A signal generator and LED are used to generate the excitation signal that is first guided through a filter and then through a coated and unclad fiber optic cable mounted in a gas flow cell. Escaping light excites the coated dye on the cable which, in turn, emits a certain intensity of light related to the concentration of the oxygen sample. The emitted light is then directed through a second filter and to a light detector via a collecting lens. The output of the detector is amplified and read out on an instrument.

The signal generator, LED, lens, filter, detector, amplifier and other components of prior art sensor systems require a significant amount of space and, as such, are typically reserved for the laboratory or research facility. Such systems require special mounting apparatuses, are expensive to build and maintain and cannot be used in most field applications. Moreover, the detecting capability of such systems depends primarily on the amount of emission light which eventually reaches the detector. Light losses, however, are experienced with each stage of the setup placing a premium on the strength of the light source as well as the sensitivity of the detector. Also, the overall bulkiness and high number of components limits their use in most practical field applications. From a manufacturing standpoint, the prior art systems are expensive to build.

SUMMARY OF THE INVENTION

The use of fluorescence-based sensor systems in most practical field applications has been a problem. The recent availability of low cost high intensity light sources and miniaturized detector components, however, has allowed the design of more compact and miniaturized fluorescence-based sensors. A miniaturized system would provide significant advantages over the bulkier prior art systems typically reserved for the laboratory and research environment.

Accordingly, it is a primary object of the present invention to provide a miniaturized integrated fluorescence sensor for use in the field. In this regard, a sensor that leverages of known biochemical interactions between one or more fluorescent assays and a given sample is disclosed.

In one embodiment, a thin film of the fluorophore material is deposited on a surface of an encapsulating housing which functions as an optical substrate. The fluorophore can be deposited using known processes such as dip coating, spin coating, pad printing or vapor phase deposition. A light emitting diode generates the excitation energy required by the fluorophore which, in turn, emits a certain intensity emission signal in the presence of the sample.

Another object of the present invention is to provide a sensor that increases the detector's ability to resolve the information content of the emission energy. In this regard, optical separation of the emission light from scattered sources of excitation light is achieved by placing one or more filters at prearranged spatial positions within the housing. This is accomplished by shaping the platform to optically divert excitation light away from the detector. In one embodiment, the platform is coated with a light absorbent material to create an optical sink to the stray excitation light. In another embodiment, the geometric configuration of the housing diverts excitation light incident to sensor surfaces away from the detector's reception area increasing the sensor's separation figure of merit.

Yet another object of the present invention is to provide a low cost easy to manufacture sensor platform that can be easily interfaced to existing processing equipment such as a personal computer, hand held instrument or other similar equipment. This is achieved by embedding the light source, the detector and other sensor components on a single device platform which is encapsulated in a hardened light transmissive housing. In one embodiment, the bottom of the platform has pins that provide an interface to the outside world. Power is coupled to the LED via the pins and signal data can be transferred from the detector to an external system for further analysis.

In yet another embodiment, an integrated biochemical sensor for detecting the presence of one or more specific samples is disclosed. The sensor has a platform with a light absorbing top surface and a bottom surface with pins extending therethrough that interface the output of the sensor detector to an external processing system. A light transmissive encapsulant provides the optical transmission medium and covers the platform and all of the sensor components coupled thereto. A layer of fluorescence chemistry is deposited on a surface of the housing and a LED provides the excitation light required by the chemistry and is directed at the chemistry layer using the optical properties of the housing and one or more filter elements. In other embodiments, a reflective mirror and focusing surface are used.

For a more complete understanding of the present invention, including its features and advantages, reference is now made to the following detailed description, taken in conjunction with the accompanying drawings.

BRIEF DESCRIPTION OF THE DRAWINGS

In the drawings:

FIG. 1 depicts a prior art sensor system using a fluorescent coated fiber optic cable;

FIGS. 2A and 2B depict a practical laboratory set-up using fluorescent-based prior art sensor technology;

Corresponding numerals and symbols in the different figures refer to corresponding parts unless otherwise indicated.

DETAILED DESCRIPTION OF THE PREFERRED EMBODIMENT

Figure 3:
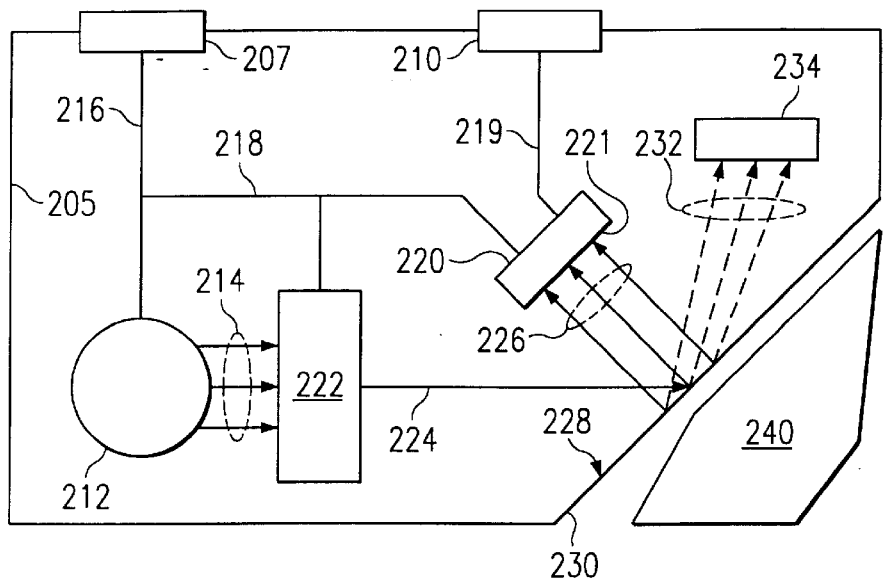
FIG. 3 is a block diagram of a first embodiment of a fluorescent-based sensor in accordance with the invention.

Referring now to FIG. 1, a block diagram of a prior art system used in fluorescence-based sensing applications is shown and denoted generally as 10. System 10 includes a signal generator 15 which provides an excitation signal of appropriate wavelength and amplitude depending on the fluorescence chemistry selected. A particular chemistry is chosen based on the particular sample of interest. The chemistries and their properties are well known in the art.

Coupled to the signal generator 15 is light source 20 which in one prior art system constitutes a single high brightness blue Light Emitting Diode (LED). Light source 20 is chosen for its wavelength characteristics and provides the excitation energy required by the chemistry layer. Light signals from light source 20 are focused by collimating lens 25 and directed towards the coated fiber cable 40. A cut off filter 30 is used to block out unwanted light frequencies.

The excitation signal from light source 20 is transferred into a launching lens 35 before reaching the coated fiber cable 40. When the particular sample, i.e., oxygen, carbon dioxide, nitrate, alcohols and others, is placed in contact with the coated fiber cable 40, the character of fluorescence emission changes in intensity. This change can be detected and measured by well known methods. Thus, the output signal of light source 20 excites the chemical coating on fiber cable 40 and the chemistry layer, in turn, when exposed to the sample, emits a certain intensity of light which is related to the sample concentration.

A small portion of this emission light is gathered by collecting lens 45 and directed towards filter 50. In one known embodiment, filter 50 is a 610 nm cut-on filter which works together with the collecting lens 45 to direct the emission light to detector 55. A photo multiplier tube or silicon photo diode can be used as a suitable detector 55.

The emission light generated by the presence of a sample near the coated fiber cable is sensed by the detector 55 and the output from the detector 55 is directed into lock-in-amplifier 60 wherein the emission signal is amplified for processing by system 65. The processing system 65 can be a personal computer, expert system or other similar device used to monitor the detector 55 output.

Turning now to FIG. 2, a prior art laboratory sensing system 10 is shown and denoted generally as 70. Light source 75 emits a light energy 80 of a predetermined intensity and wavelength. A LED, laser, incandescent lamp or other similar source of light are suitable components for light source 75.

As shown, the light energy 80 is directed into lens 85 which focuses, directs and guides the light energy into cable 90 or some other point of interest. A signal splitter 95 directs a measuring sample of the light energy 80 into instrument 105 via cable 100 and allows instrument 105 to track and monitor signal strength and presence.

Light energy 80 is transmitted via connector 110 and probe length 115 into instrument 120 which performs the sensing and detection functions. A coated fiber sensor 135 is inserted into a liquid sample 130. For one embodiment sensor 135 is coated with fluorescence emitting chemical known to react in the presence of sample 130. The overall intensity of the fluorescence radiation is small, however, compared to the excitation light energy 80.

As shown, the sensor 135 has core 140 which is coated with a fluorescence assay known to interact with the particular sample 130. A sample reading of the radiated emission light energy is received by instrument 105, via sensor 135 and probe 150. The presence of the sample 130 can be visually confirmed on instrument 105. Sensor system 70 can be configured to detect gases, solids and given molecular properties of a solution or compound.

Turning now to FIG. 3, a block diagram of an integrated fluorescent-based sensor according to the invention is shown and denoted generally as 200. FIG. 3 shows that various sensor components are enclosed inside a light transmissive housing 205. Interfaces 207 and 210 are coupled to housing 205 and provide communications paths between the sensor 200 and the outside world. In one embodiment, interface 207 is used to provide an outside source of power to the sensor 200 while interface 210 is the output from the detector 220.

As shown, interface 207 is coupled to various sensor components via paths 216 and 218 and the detector 220 is coupled to interface 210 via path 219.

A sample 240, such as a gas or liquid solution, is brought in contact with the sensing surface 228 causing an interaction of the fluorescent chemistry 230 with the sample 240. The fluorescence chemistry 230 has been deposited on sensing surface 228 and arranged on the sensor 200 at a predetermined angular orientation to the excitation energy 224. The fluorescence coating 230 may be deposited by one of various processes such as dipping, spin coating, pad printing or vapor phase deposition all of which are well known in the art. In one embodiment, chemistry layer 230 consists of a thin film of fluorescence chemistry which interacts with sample 300 to emit light energy 226. The emission light 226 is directed towards detector 220 which is fixed within the housing 205 at a predetermined location.

The excitation energy required by the fluorescence chemistry 230 is provided by light sources 212. Various sources of radiation may be employed including a light emitting diode, laser or miniaturized incandescent lamp. Other forms of light are also envisioned. Power to the sensor 200 is supplied via lead 216 from the interface 207.

The excitation energy 214 from the light source 212 is directed at the optical configuration 222 which can be one or more optic lens(es) or focusing surface(s) of the housing 205. In one embodiment, a radiation energy peak wavelength of approximately 450 nm with a full width at half maximum of approximately 80 nm has been sufficient to ensure adequate coupling of the excitation light 214 onto the chemistry the layer 230.

As shown, the optical configuration 222 provides a light directing means that directs energy 214 from the light source 212 to the chemistry layer 230. The excitation light 224 interacts with the chemistry 230 to produce fluorescence emissions 226 in the presence of sample 240. As shown, platform 228 is angularly positioned to direct excess excitation energy away from the detector 220 and towards blocking filter 234. This gives the sensor 200 a high separation figure of merit as described herein.

The character of the fluorescence emission 226 is altered in the presence of sample 240 resulting in a lower intensity radiation compared to that of excitation light 214. The sensing surface 228 is spatially arranged with respect to the detector 220 to ensure a sufficient amount of emission light 226 reaches the receiving surface 221 of the detector 220 and thereby minimizing the incidence of primary excitation light 222 onto detector surface 221.

The optical sink 234 absorbs the reflected excitation light 232 increasing the detectors ability to resolve the incoming emission light 226 related to the sample of interest 240. The optical sink 234 may comprise a light absorbing material which coats the housing 205 and directs the stray excitation light 232 outward from the housing 205. Alternatively, optical sink 234 is a distinct sub-assembly within the housing 234 placed in the path of the excitation light 232 which redirects light incident away from the detector 220.

In theory, total optical separation of the scattered light 234 from the emission light 226 would be ideal. In practice complete separation may not be realistic. A measure of the effectiveness of a sensor's ability to separate excitation energy from the emission energy is known as the Separation Figure of Merit ("SFM"). The SFM and underlying principle on which the present invention relies on are understood by those skilled in the art as follows:

Theory of Operation—Fluorescence "Separation Figure of Merit"

Definitions

EX=Excitation Light

EM=Emission Light $f_{EX}$=Fraction of Excitation Light which hits detector $f_{EM}$=Fraction of Emission Light which hits detector $\eta$=efficiency or # of Emissions Photons per Excitation Photon R=Amount of Light Detected.

So (EM)=$\eta$(EX); $\eta$->1 is desirable

However, $\eta$ is a variable which reflects, or quantifies the amount of a particular gas.

e.g. For the case of a Ruthenium fluorophore: $\eta$=F [$O_2$]

Since $\eta$->Em, Em ->Large is desirable

To detect Em, we would like $f_{EM}$->1

It is often the case that $\eta<<1$, so:

EX >>Em

The detector "sees": $f_{EX}(Ex) + f_{EM}(Em) = R = f_{EX}(Ex) + f_{EM}\eta(Ex)$ $$\rightarrow R = (Ex)[f_{EX} + f_{EM}\eta] = (Ex)f_{EM}\left[\eta + \frac{f_{EX}}{f_{EM}}\right]$$

Since $\eta$ contains the information of interest, $f_{EX}$ $$\frac{f_{EX}}{f_{EM}} << \eta$$

Recall that it is often the case that $\eta<<1$, $$\frac{f_{EX}}{f_{EM}} << <<1,$$

When this condition is satisfied, we define the system to have total optical separation.

The attempt, or success, at approaching this in an integrated, or semi-integrated, small fluorescence sensor is the subject of the present invention.

It is clear that the objective is to have to be as small as possible.

$$\frac{f_{EX}}{f_{EM}}$$

Whether the condition of $$\frac{f_{EX}}{f_{EM}} << <<1,$$

or total optional separation, is satisfied, means of minimizing $$\frac{f_{EX}}{f_{EM}}$$

will be considered to be part of the present invention when included in a fluorescence sensor design.

In the spherical dome embodiment (i.e. FIGS. 6 and 7), light tracing clearly demonstrates that the optical design is such that a significant proportion of Ex is directed away from the detector. This portion of Ex is that which does not result in Emission and is reflected back into the device from the outer curved surface at an angle of reflection equal to the original angle of incidence $$\rightarrow \text{Minimization of } f_{EX} \rightarrow \frac{f_{EX}}{f_{EM}}$$

is made smaller.

At the same time, the emission cross-section will be most intense in a direction normal to the domed surface. Such directed light will be directly incident upon the detector, hence $$\text{maximizing } f_{EM} \rightarrow \frac{f_{EX}}{f_{EM}}$$

is made smaller.

While FIG. 3 illustrates a model sensor according to one embodiment of the invention, it should be understood that the individual components and functions thereof may be rearranged, combined or modified to achieve equivalence in function with the embodiment shown. For example, in contemplated variations of the invention, the light guide 222 and platform 228 are integrated molded surfaces of the housing 205. In another variation, one or more filter elements are included to help block stray light emissions from the detector surface 221. Other variations will become apparent to those skilled in the art.

Figure 4:
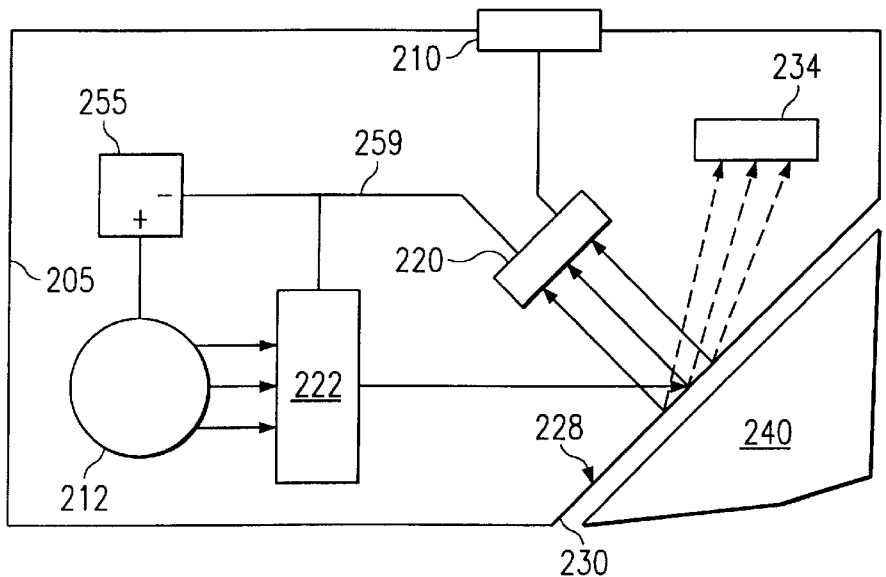
FIG. 4 is a block diagram of a second embodiment of a fluorescent-based sensor in accordance with the invention.
Figure 5:
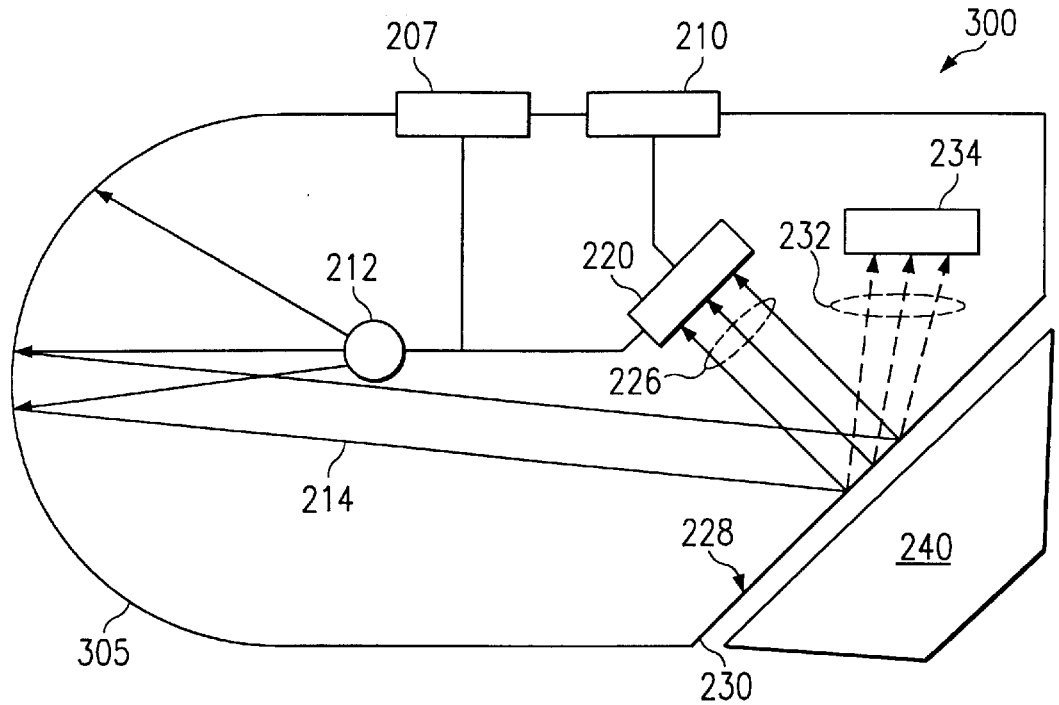
FIG. 5 is a block diagram of a third embodiment of a fluorescent-based sensor in accordance with the invention.

FIGS. 4 and 5 illustrate alternative embodiments of the integrated fluorescence-based sensor shown in FIG. 3. The sensor configuration of FIG. 4, denoted generally as 250, is similar to sensor 200 but contains an onboard power supply 255 operably coupled to the light source 212 via path 257 and to the detector 220 via path 259. As contemplated herein, sensor 250 has application in areas where power is unavailable such as in the field or where the sample 240 is located in remote and hard to reach areas.

The power source 255 may be implemented in a various configurations all of which are well known in the art. For example, power source 255 may take the form of a lithium cell battery which is placed inside the housing 205 during manufacturing. In such a case, the useful life of the sensor 250 would be the same as the cell life of power source 255. Yet in another embodiment, power source 255 is a rechargeable battery cell or a replaceable source of power.

Another variation of the invention is illustrated in FIG. 5, wherein a sensor 300 having a housing 205 with a substantially rounded mirrored surface 305 and a sensing surface 228 is shown. The mirrored surface 305 focuses the excitation energy 214 directly to the chemistry layer 230 on surface 228. As with the original sensor 200, the stray excitation light 232 and emission light 226 are separated to increase detector 220 sensitivity. The surface 307 is coated with the fluorescence chemistry and optically directs the excess excitation light away from the detector 220 and towards optical sink 234.

Sensor 300 provides lower component count and increased ease of manufacture. As with the sensor 200, interfaces 207 and 210 are provided as signal conduits between the internal sensor components and the outside world. Also, in another embodiment sensor 300 is fitted with an onboard power source similar to that of FIG. 4.

Figure 6:
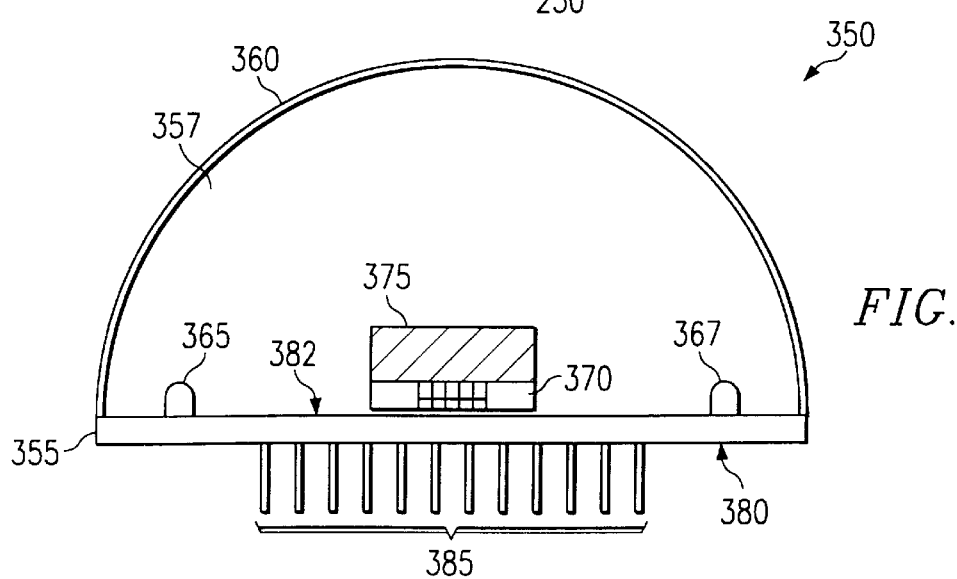
FIG. 6 is a side profile view of a miniaturized integrated fluorescence sensor according to the invention.

Turning to FIG. 6, a side profile view of a miniaturized integrated fluorescent-based sensor in accordance with one embodiment of the invention is shown and denoted generally as 350. Sensor 350 has a device platform 355 with an upper surface 382 to which the various device components are coupled. A semi-sphere encapsulating enclosure 357 is coupled to the platform 355 and forms a sensor housing which permits light to be transmitted within the housing body. The differences in refractive index between the enclosure 357 material and the outside world assure that internally generated light is reflected towards the detector 370 which sits adjacent to one or more light sources 365 and 367 on the upper surface 382 of the platform 355.

Preferably, the device platform 355 is made of a light absorbing epoxy substrate while enclosure 357 is made from a light transmissive material such as a hardened polyurethane. Other suitable materials include glass, PCB or ceramic. Likewise, the platform 355 may be manufactured from a suitable metallic substance such as copper, steel, alloy or other plated material with a light absorbing top surface layer deposited thereon. Still other materials and methods of manufacture are within the scope of the invention.

The outer surface 360 of the enclosure 357 is coated with a thin film of fluorescence chemistry selected from any one of a plurality of number of chemical reactants which are well known in the art. The choice of chemistry depends primarily on the sample to be identified and as such, the invention embodies a wide variety of chemistry/sample combinations.

For example, a sensor capable of detecting oxygen could be implemented using a Ruthenium-based chemistry layer. The Ruthenium indicator can embedded in a matrix such as a polymer or a sol-gel layer and deposited on the surface 360 by well known methods such as spin coating, dip coating, pad printing, vapor deposition or other similar processes. As is well known in the art, a blue light emitting diode would can be used to provide the excitation signal for Ruthenium.

As shown in the profile of FIG. 6, sensor 350 has light sources 365 and 367 coupled to the device platform 355 and completely immersed within the enclosure 357. In the preferred embodiment, light sources 365 and 367 are miniaturized blue LEDS of the type readily available in the marketplace, although other forms of light radiation may be used.

The light emissions from light sources 365 and 367 travel to surface 360 and interact with the fluorescence chemistry thereon. Since the enclosure 357 is optically transmissive, the light generated by light sources 365 and 367 reaches the surface 360 substantially uniformly.

The excitation energy emitted by light sources 365 and 367 reaches outer surface 360 and interacts with the fluorescence deposit thereon. At this point, some of the excitation light will be absorbed by the fluorophore while some of the light will be reflected back into the interior portion of the enclosure 357 and away from the detector 370. Thus, as sensor 350 is brought in contact with the sample, the chemical deposit on outer surface 360 causes an emission light energy to be generated which travels into the enclosure 357 body in the direction of the detector 370.

As shown, a filter element 375 is positioned on the detector 370 and arranged to block any scattered excitation light from the detector 370. This arrangement increases detector 370 sensitivity and its ability to resolve incoming emission energy which can be small compared to the excitation light.

Detector 370 may be implemented using a wide variety of available devices and component configurations. One example would be a photo diode in combination with an operational amplifier. A light to frequency converter may also be used to provide a digitized output signal. A suitable device for this purpose is the TSL230, a three contact silicon integrated circuit. In other embodiments, a programmable light-to-voltage converter, such as the TSL250, may be used as a detector 370. Other combinations of detector components and elements are within the scope of the invention.

An interface 385 is coupled to bottom surface 380 of the sensor 350 and provides a communications pathway between the sensor 350 and the outside world. Examples of the interface 385 signals include power, detector output, and reference.

Figure 7:
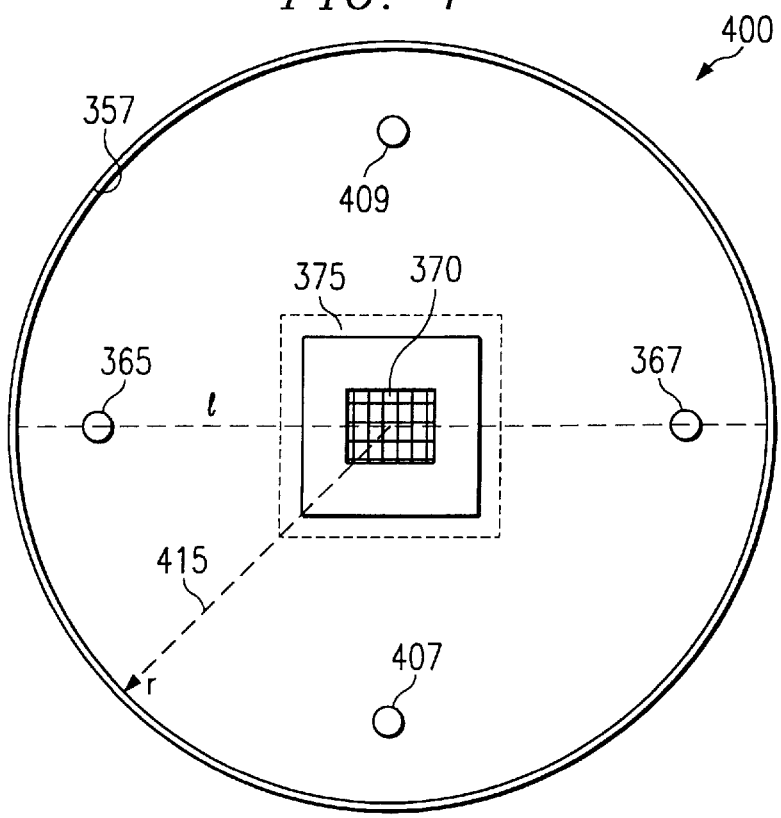
FIG. 7 is a top down view of the miniaturized integrated fluorescence sensor depicted in FIG. 6.

FIG. 7 is a top down view 400 of the sensor 350 shown in FIG. 6. As shown, light sources 365 and 367 are specially arranged at an equal distance from the center of the detector 370 about line 405 which bisects the perimeter of enclosure 357. Also shown are light sources 407 and 409 which are similarly positioned from the center of detector 370 but about an axial line perpendicular to line 405. The physical location of the detector 370 and light sources 365, 367, 407, and 409 provide a uniform spread of radiation about the-surface 360 permitting a peak amplitude of emission to reach the detector 370.

Radii 415 is substantially longer than the dimensions of the detector 370. This allows a focus of the emission energy to the detector 370 and a minimization of the incidence of reflected excitation light onto the detector 370. In one embodiment, the radii 415 is at least five (5) times the width or length of detector 370, although other proportions are within the scope of the invention.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. Specifically, and as contemplated by the inventors, the use of more than one sensing surface is envisioned wherein the reflected excitation light directed away from the detector is used to excite one or more additional sensing surfaces to obtain more sample data. Also envisioned is the use of the sensor configuration, as herein described, in chemiluminescence sensing applications wherein no excitation light source is required to excite an emission. It is therefore intended that the appended claims encompass any such modifications and/or embodiments.

What is claimed is:

1. A sensor assembly comprising:

a platform having an upper surface and a bottom surface;

a light source coupled to the upper surface of the platform;

a detector coupled to the upper surface of the platform adjacent the light source; and an encapsulating housing extending over the platform and arranged to receive light from the light source;

where at least a portion of the exterior surface of the housing has a fluorescence emitting chemistry layer disposed upon it to form a sensing surface, the fluorescence emitting chemistry layer has a characteristic quality that interacts with a specific analyte sample to produce a change in the layer's fluorescence emission;

where the light source emits light having an wavelength that excites the fluorescence emitting chemistry layer; and where the housing has a substantially dome-shaped portion, the dome-shaped portion having a location and a radius such that the normal direction of the surface of the dome-shaped portion is oriented towards the detector, thereby increasing the amount of light emitted from the fluorescence emitting chemistry layer that impinges upon the detector.

2. An integrated miniaturized sensor for indicating the presence of a given analyte sample comprising:

a first light source;

a sensing surface spatially arranged about the first light source to receive light;

a detector mounted proximate the first light source and positioned to intercept light emitted from the sensing surface; and a light transmissive housing encapsulating the first light source and the detector;

wherein, the exterior of the housing includes the sensing surface, and the housing is shaped to reflect light from the first light source away from the detector and toward an optical sink.

3. The integrated miniaturized sensor according to claim 2, wherein the sensing surface portion of the housing is substantially dome-shaped, the dome-shaped portion of the housing approximately centered on the detector.

4. The sensor according to claim 3, further including second, third and fourth light sources spatially arranged with respect to the first light source and each other to uniformly distribute light about the housing.

5. The integrated miniaturized sensor according to claim 2, further comprising a platform with an upper surface and a bottom surface, the upper surface coupled to the first light source, the sensing surface, the detector and the optical sink, the upper surface being coated with a light absorbing material.

6. The sensor according to claim 5, further comprising an interface coupled to the bottom surface of the platform.

7. A fluorescence-based sensor for selectively identifying the presence of oxygen comprising:

a platform having an upper and a bottom surface;

a blue light emitting diode coupled to the upper surface of the platform;

a photodiode coupled to the upper surface of the platform adjacent the diode; and an encapsulating housing extending over the upper surface of the platform, the housing having an outer portion with a ruthenium-based fluorescing chemistry thereon, the outer portion spatially arranged to:

receive light from the diode, thereby exciting the fluorescing chemistry, reflect a substantial portion of the light received from the diode away from the photodiode; and allow light from the fluorescing chemistry to impinge upon the photodiode.

8. The sensor according to claim 7, further comprising an optical sink arranged within the housing to minimize the light from the diode which is incident upon the photodiode.

9. The sensor according to claim 7, wherein the ruthenium-based chemistry exists in a sol-gel chemistry layer.

* * * * *